US010444247B2

(12) United States Patent
Hurskainen et al.

(10) Patent No.: US 10,444,247 B2
(45) Date of Patent: Oct. 15, 2019

(54) METHOD FOR DETERMINING THE RISK OF PRETERM BIRTH

(71) Applicant: Wallac Oy, Turku (FI)

(72) Inventors: Pertti Hurskainen, Piispanristi (FI); Heikki Kouru, Raisio (FI); Mikko Sairanen, Masku (FI); Tarja Ahola, Turku (FI); Teemu Korpimäki, Paimio (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 15/512,190

(22) PCT Filed: Sep. 11, 2015

(86) PCT No.: PCT/FI2015/050594
§ 371 (c)(1),
(2) Date: Mar. 17, 2017

(87) PCT Pub. No.: WO2016/042202
PCT Pub. Date: Mar. 24, 2016

(65) Prior Publication Data
US 2017/0261511 A1 Sep. 14, 2017

(30) Foreign Application Priority Data
Sep. 17, 2014 (FI) .................................... 20145815

(51) Int. Cl.
*G01N 33/68* (2006.01)
*G01N 33/53* (2006.01)

(52) U.S. Cl.
CPC ..... *G01N 33/689* (2013.01); *G01N 2800/368* (2013.01)

(58) Field of Classification Search
None
See application file for complete search history.

(56) References Cited

U.S. PATENT DOCUMENTS

| | | | | |
|---|---|---|---|---|
| 4,208,479 A * | 6/1980 | Zuk | ...................... | C07J 41/0016 435/7.72 |
| 5,545,616 A * | 8/1996 | Woodruff | ........... | A61K 38/1709 514/8.9 |
| 7,666,583 B2 | 2/2010 | Mor et al. | | |
| 2010/0304978 A1* | 12/2010 | Deng | ................... | C12Q 1/6879 506/7 |
| 2012/0115226 A1* | 5/2012 | Stachelsheid | .......... | C12M 25/10 435/366 |
| 2013/0177901 A1 | 7/2013 | Darbouret et al. | | |
| 2014/0113876 A1* | 4/2014 | Chan | .................... | C12Q 1/6883 514/23 |
| 2014/0186332 A1* | 7/2014 | Ezrin | ................... | G01N 33/689 424/130.1 |
| 2014/0220580 A1* | 8/2014 | Brown | ............ | G01N 33/57434 435/6.12 |
| 2014/0324460 A1* | 10/2014 | Caffrey | ............... | G06F 19/3431 705/3 |

FOREIGN PATENT DOCUMENTS

| | | |
|---|---|---|
| WO | 2009094665 A1 | 7/2009 |
| WO | 2009152601 A1 | 12/2009 |
| WO | 2011068956 A2 | 6/2011 |
| WO | 20150173430 A2 | 11/2015 |

OTHER PUBLICATIONS

Valerio et al. ( Minerva. Ginecol. 1996 vol. 48: 169-173) (Year: 1996).*
Petraglia et al. J. Endocrinology 1997 vol. 154, p. 95-101 (Year: 1997).*
Finnish Patent and Registration Office, Search Report issued on FI20145815, dated Apr. 20, 2015.
Spencer, K., "Second-trimester prenatal screening for Down syndrome and the relationship of maternal serum biochemical markers for pregnancy complications with adverse outcome". Prenatal Diagnosis, Aug. 2000, vol. 20, No. 8, pp. 648-651. <DOI: 10.1002/1097-0223(200008)20:8<652::AID-PD882>3.0.CO;2-6>.
Cohen, J. L. et al., "Predictive value of combined serum biomarkers for adverse pregnancy outcomes". European Journal of Obstetrics & Gynecology and Reproductive Biology, Oct. 2014, vol. 181, pp. 89-94. Available from the Internet (Epub): 31.07.2014. <DOI: 10.1016/j.ejogrb.2014.07.018>.
Yaron, Y. et al., "Second-trimester maternal serum marker screening: maternal serum alpha-fetoprotein, beta-human chorionic gonadotropin, estrio, and their various combinations as predictors of predictors of pregnancy outcome". American Journal of Obstetrics & Gynecology, Oct. 1999, vol. 181, No. 4, pp. 968-974. <DOI: 10.1016/S0002-9378(99)70334-0>.
Han, X. et al., "Serum Follistatin-like-3 was elevated in second trimester of pregnant women who sugsequently developed preeclampsia". Hypertension in Pregnancy, Aug. 2014, vol. 33, No. 3, pp. 277-282. <DOI: 10.3109/10641955.2013.874439>.
Pryor-Koishi, K. et al., "Overproduction of the follistatin-related gene protein in the placenta and maternal serum of women with pre-eclampsia". BJOG an International Journal of Obstetrics and Gynaegology, Sep. 2007, vol. 114, No. 9, pp. 1128-1137. <DOI: 10.1111/j.1471-0528.2007.01425.x>.
Hu, D. et al., "Decreased maternal and placental concentrations of follistatin-like 3 in gestational diabetes". Clinica Chimica Acta, Mar. 2012, vol. 413, No. 5-6, pp. 533-536. <DOI: 10.1016/j.cca. 2011.10.029>.

(Continued)

*Primary Examiner* — Changhwa J Cheu
(74) *Attorney, Agent, or Firm* — Berggren LLP

(57) ABSTRACT

The present invention relates to a method for determining risk of preterm birth (PTB) in a pregnant individual. The method comprises measuring in a biological sample obtained from the pregnant individual, levels of biomarkers AFP and free hCGbeta, and at least one biomarker selected from FSTL3, sTNR1, P1GF2, Activin A, Ue3 and sP-selectin and optionally cervical length; or levels of biomarkers AFP and free hCGbeta and cervical length, and determining a relative risk of the pregnant individual developing PTB. The invention relates also to a kit, apparatus and system for predicting risk of PTB.

6 Claims, 7 Drawing Sheets

(56) References Cited

OTHER PUBLICATIONS

Blencowe, H. et al., "Born Too Soon: The golbal epidemiology of 15 million preterm births". Reproductive Health 2013, 10(Suppl 1):S2, Nov. 15, 2013 [serial online], [retrieved on Apr. 15, 2015]. Retrieved from the Internet: <URL:http://www.reproductive-health-journal.com/content/10/S1/S2>. <DOI: 10.1186/1742-4755-10-S1-S2>.

Jelliffe-Pawlowski, Laura L. et al., "Second trimester serum predictors of preterm birth in a population-based sample of low-risk pregnancies", Prenatal Diagnosis, vol. 30, No. 8, Aug. 27, 2010, pp. 727-733, XP055227828, GB, ISSN: 0197-3851, DOI: 10.1002/pd.2489.

Database Biosis [Online], Biosciences Information Service, Philadelphia, PA, US; Jan. 2001, Odibo Anthony O. et al., "Does the addition of biochemical markers improve the prediction of preterm delivery by transvaginal ultrasound of the cervix?", XP002750873, Database accession No. PREV200100167466, the whole document, & American Journal of Obstetrics and Gynecology, vol. 184, No. 1, Jan. 2001, p. S36. 21st Annual Meeting of the Society for Maternal-Fetal Medicine; Reno, Nevada, USA, Feb. 5-10, 2001.

Yeast, J.D. et al., "Biochemical markers for the prediction of preterm delivery", Clinics in Perinatology, vol. 34, No. 4, Dec. 1, 2007, pp. 573-586, vi, XP009187165, ISSN: 0095-5108, DOI: 10.1016/J.CLP.2007.09.006.

Database Biosis [Online], Biosciences Information Service, Philadelphia, PA, US; Jan. 2011; Medford, Richelle et al., "Analysis of correlation between preterm labor and estriol levels early in pregnancy", XP002750874, Data accession No. PREV201100093447, the whole document, & American Journal of Obstetrics and Gynecolgy, vol. 204, No. Suppl., Jan. 1, 2011, p. S207, 31st Annual Meeting of the Society-For-Maternal-Fetal-Medicine; San Francisco, CA, USA, Feb. 7-12, 2011, ISSN: 002-9378(print).

Smith, G. C. S. et al., "Maternal and biochemical predictors of spontaneous preterm birth among nulliparous women: a systematic analysis in relation to the degree of prematurity", International Journal of Epidemiology 2006; 35: 1169-1117.

Palomaki, G. E. et al., "Maternal serum alpha-fetoprotein, age and Down syndrome risk", American Journal of Obstetrics & Gynecology 1987, vol. 156, No. 2, pp. 460-463.

Norgaard-Pedersen, B. et al., "Maternal serum markers in screening for Down syndrome", Clinical Genetics 1990: 37: 35-43.

Translation of CN Office Action issued in CN patent application No. 201580050277.8 dated Jan. 23, 2018.

European Patent Office, Communication pursuant to Article 94(3) EPC, dated May 7, 2018.

Clinical significance of TNF-α and sTNFR I in forecasting infectious associated preterm labor, Mei-fen Ma and Wei-bin Chen, Chin. J.Nosocomiol., vol. 22, No. 6, pp. 1198-1200, 2012, published on Dec. 31, 2012 Abstract provided in English.

\* cited by examiner

METHOD FOR DETERMINING THE RISK OF PRETERM BIRTH

PRIORITY

This application is a U.S. national application of PCT-application PCT/FI2015/050594 filed on Sep. 11, 2015 and claiming priority of Finnish national application FI20145815 filed on Sep. 17, 2014, the contents of all of which are incorporated herein by reference.

BACKGROUND

Preterm birth affects over a million babies each year, and is a leading cause of infant death and long-term neurological disabilities in children worldwide. The generally accepted definition of preterm birth is delivery of an infant prior to 37 weeks of pregnancy. The earlier a baby is born, the higher risk of disability, given the reduced time available for development in the womb. Medical conditions resulting from preterm birth include breathing problems, feeding difficulties, cerebral palsy, developmental delay, vision problems and hearing impairment. Although significant advancements have been made in the care of preterm infants, the prevalence of preterm birth has not been significantly reduced. Early detection of preterm birth may reduce the prevalence of this condition. Several research studies have shown correlations of certain biomarkers with risk of early delivery. However, the effectiveness of these biomarkers has been insufficient for the reliable prediction of preterm birth in a clinical setting.

SUMMARY

The description provides a method for determining risk of preterm birth (PTB) in a pregnant individual. The method involves measuring in a biological sample obtained from the pregnant individual levels of biomarkers AFP and free hCGbeta, and determining at least one additional measurement selected from the level of a biomarker selected from the group of FSTL3, sTNR1, PIGF2, Activin A, uE3 and sP-selectin, and cervical length of the pregnant individual; and determining the risk of the pregnant individual developing PTB.

In one embodiment, the method involves measuring levels of biomarkers AFP and free hCGbeta, and determining at least one additional measurement selected from the level of a biomarker selected from the group of FSTL3, sTNR1, PIGF2, Activin A, uE3 and sP-selectin. In a specific embodiment, the biomarker is selected from FSTL3 and Activin A.

In another embodiment, the method involves measuring levels of biomarkers AFP and free hCGbeta, and determining the cervical length of the pregnant individual.

The determination of the risk of PTB can be carried out by using the models, which have been established in finding the markers, or the functions, which include the following information of the models: the dependence between marker levels and likelihood and/or directly or indirectly uses the information of correlation structure or part of it with the likelihood.

In an embodiment, the determining of risk comprises deriving the likelihood ratio for PTB using a multivariate analysis based on distribution parameters derived from a set of reference data.

In an embodiment, the risk of preterm birth is a relative risk.

In an embodiment, the biological sample is selected from the group consisting of whole blood, plasma, serum, urine, vaginocervical material, and a fraction of whole blood, plasma, serum, urine or vaginocervical material.

In an embodiment, the biological sample is obtained during weeks 11 to 13. In another embodiment, the biological sample is obtained during weeks 14 to 16. In a further embodiment, the biological sample is obtained during weeks 17-20.

In an embodiment, the gestational age of the preterm birth is less than 34 weeks.

Also provided is an in vitro kit for determining the risk of preterm birth (PTB), including means for assaying a biological sample from the pregnant individual for biomarkers AFP, and free hCGbeta, and at least one biomarker selected from the group of FSTL3, sTNR1, PIGF2, Activin A, Ue3 and sP-selectin.

Further provided is an apparatus for predicting risk of preterm birth (PTB) in a pregnant individual. The apparatus includes a data input means for inputting a measurement of a biological sample of the pregnant individual for biomarkers AFP and free hCGbeta, and at least one biomarker selected from the group of FSTL3, sTNR1, PIGF2, Activin A, Ue3, sP-selectin, and cervical length; or for biomarkers AFP and free hCGbeta and measurement of biophysical marker cervical length; and calculation means for determining the risk of PTB using the input levels of the said biomarkers.

In the following text, the invention will be further described with the aid of a detailed description and with reference to some working examples.

DETAILED DESCRIPTION

Figure 1:
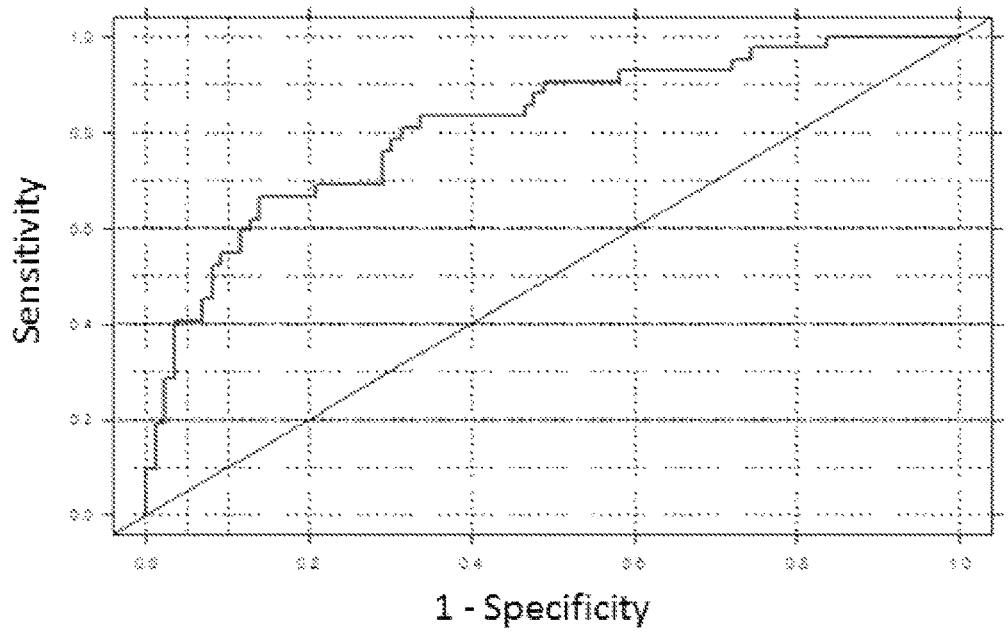
FIG. 1 shows the screening performance of AFP, fhCGbeta and FSTL3. Preterm birth<37 weeks FIG. 2 describes the screening performance of AFP, fhCGbeta and PIGF-2 Preterm birth<37 weeks FIG. 3 describes the screening performance of AFP, fhCGbeta and sTNFR1. Preterm birth<37 weeks FIG. 4 describes the screening performance of AFP, fhCGbeta and FSTL3. Preterm birth, GA=34-36 weeks FIG. 5 describes the screening performance of AFP, fhCGbeta and PIGF-2. Preterm birth, GA=34-36 weeks FIG. 6 describes the screening performance of AFP, fhCGbeta and sTNFR1. Preterm birth, GA=34-36 weeks FIG. 7 describes the screening performance of AFP, fhCGbeta and FSTL3. Early Preterm birth, GA<34 weeks FIG. 8 describes the screening performance of AFP, fhCGbeta and PIGF-2. Early Preterm birth, GA<34 weeks FIG. 9 describes the screening performance of AFP, fhCGbeta and sTNFR1. Early Preterm birth, GA<34 weeks FIG. 10 describes the screening performance of AFP, fhCGbeta and Activin A. Early Preterm birth, GA<34 weeks FIG. 11 describes the screening performance of AFP, fhCGbeta and cervical length in all preterm birth pregnancies (including spontaneous preterm birth and premature rupture of membranes (PROM)).
Figure 2:
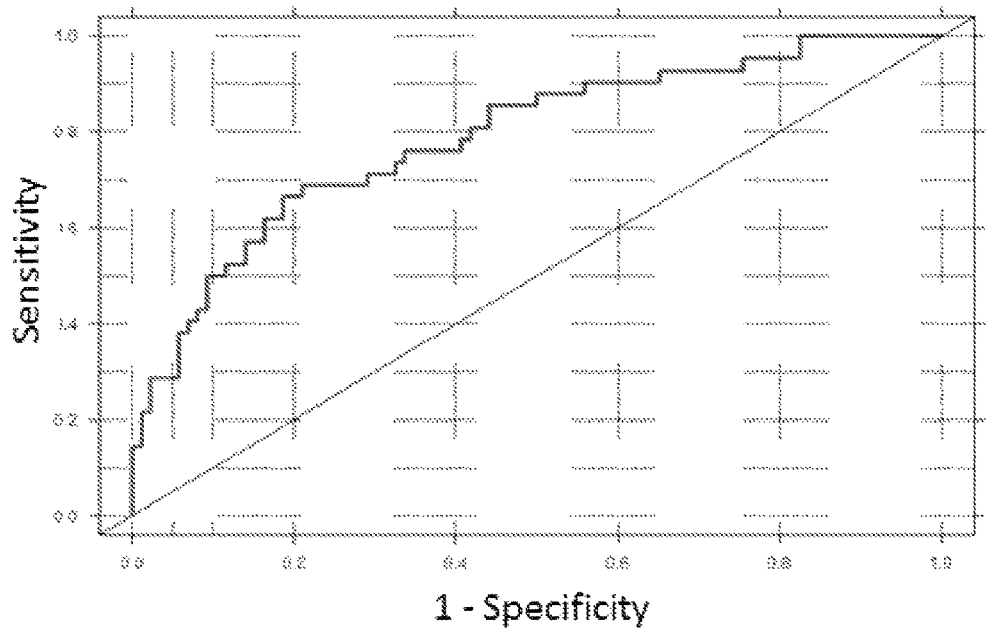
Figure 3:
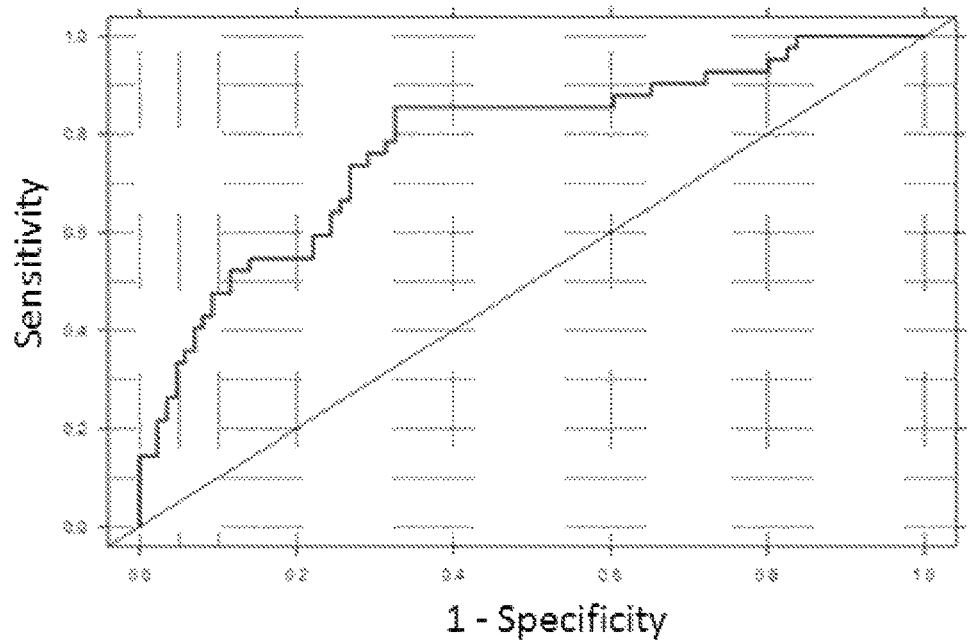
Figure 4:
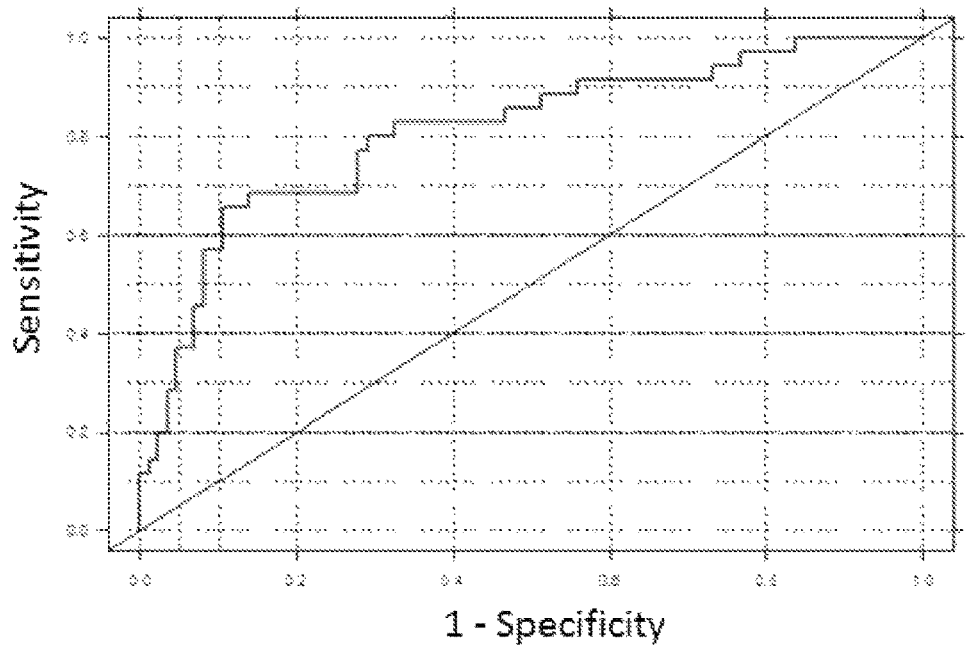
Figure 5:
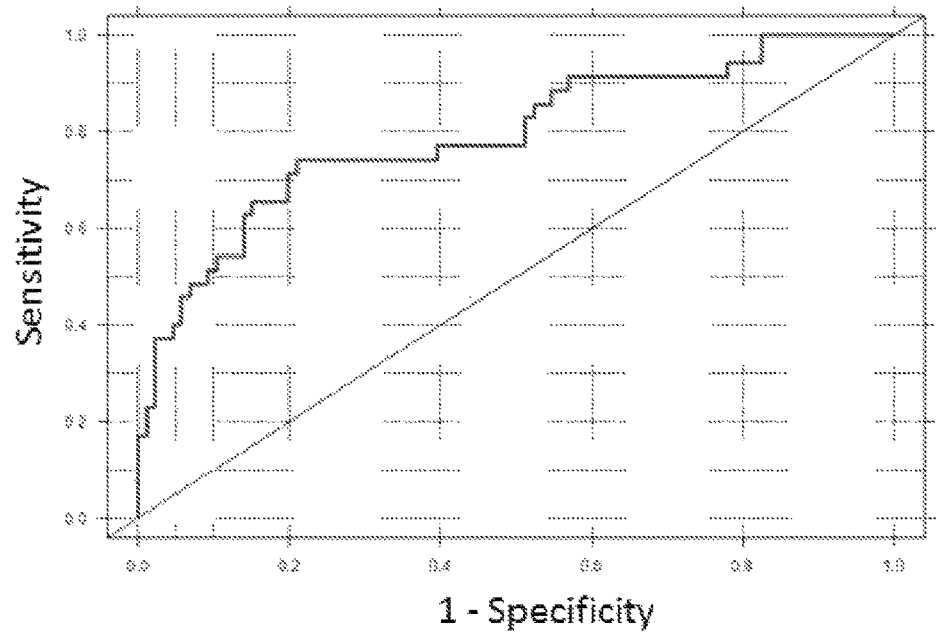
Figure 6:
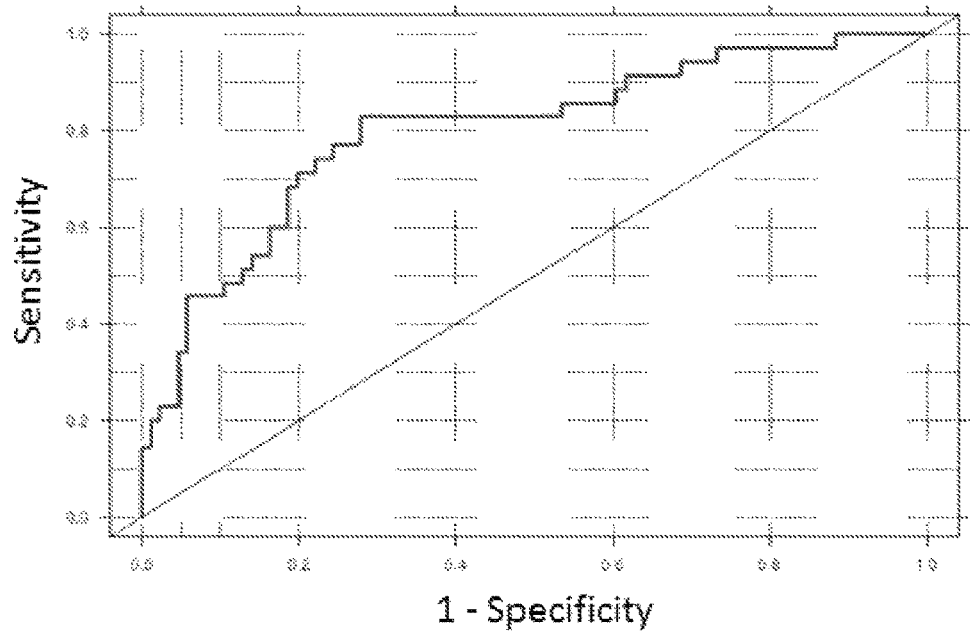
Figure 7:
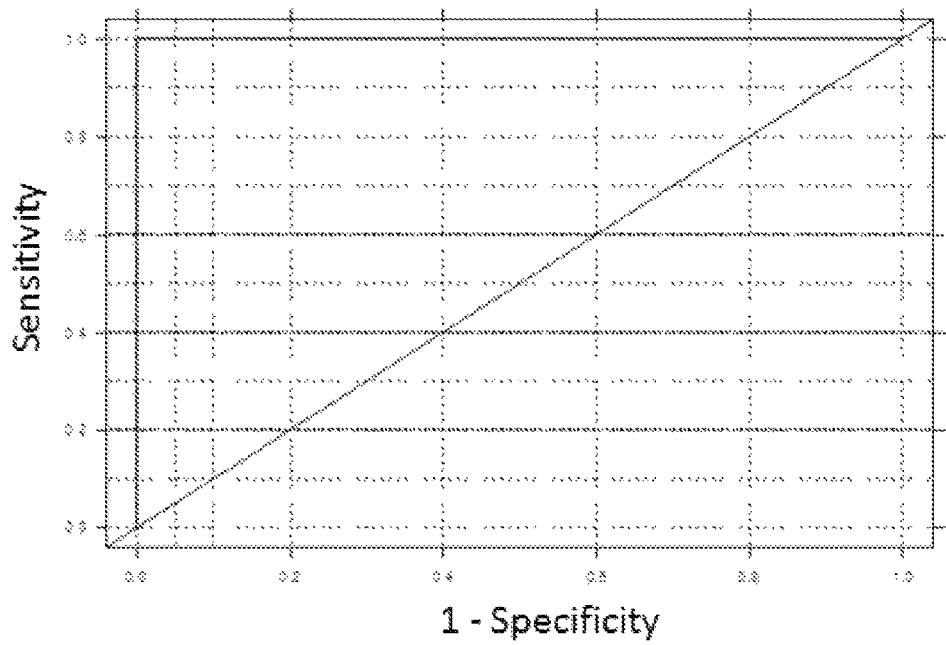
Figure 8:
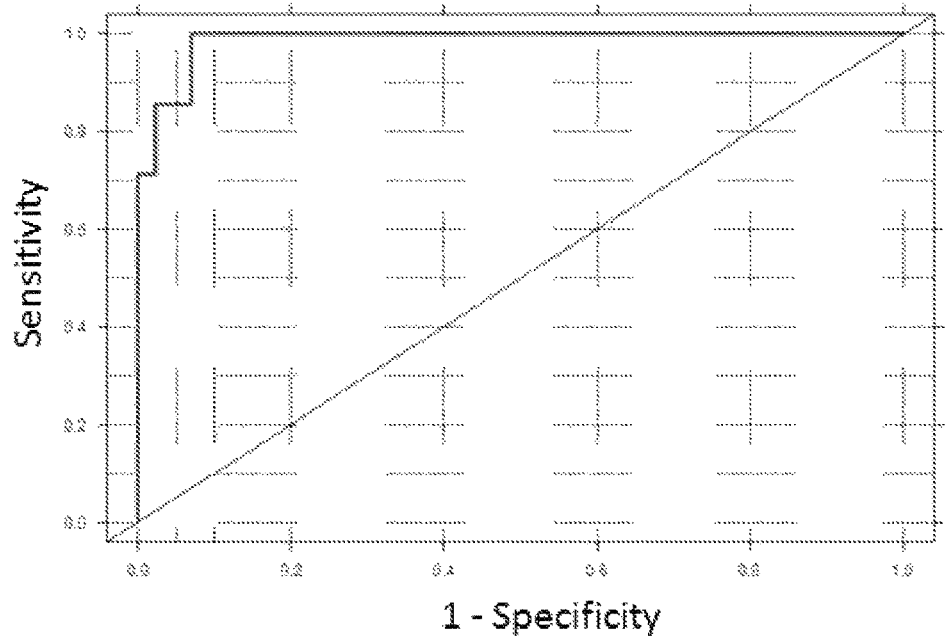
Figure 9:
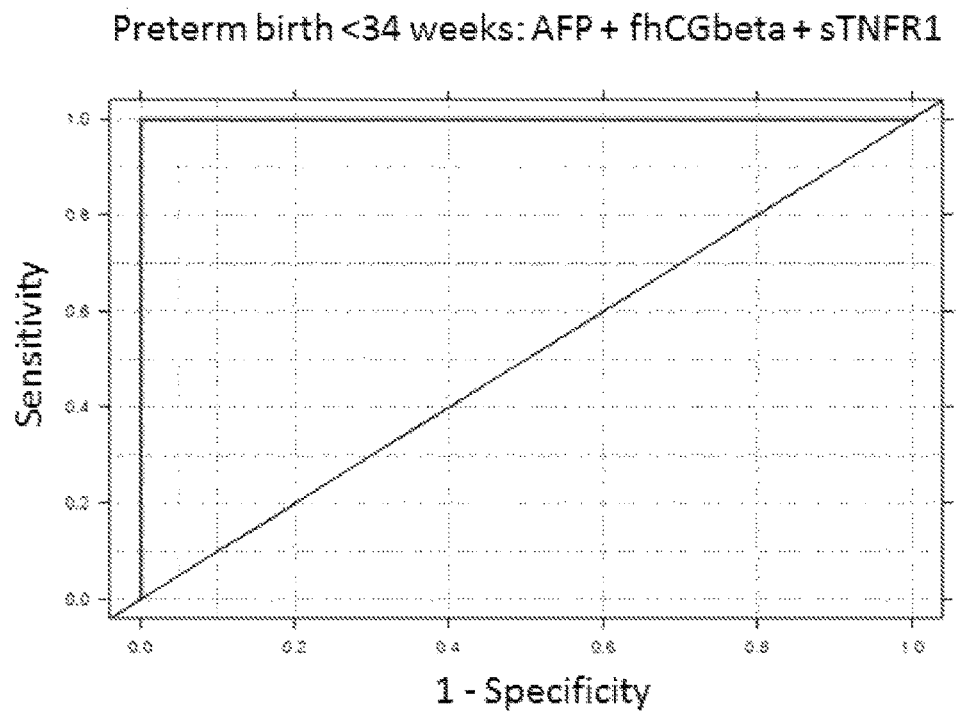
Figure 10:
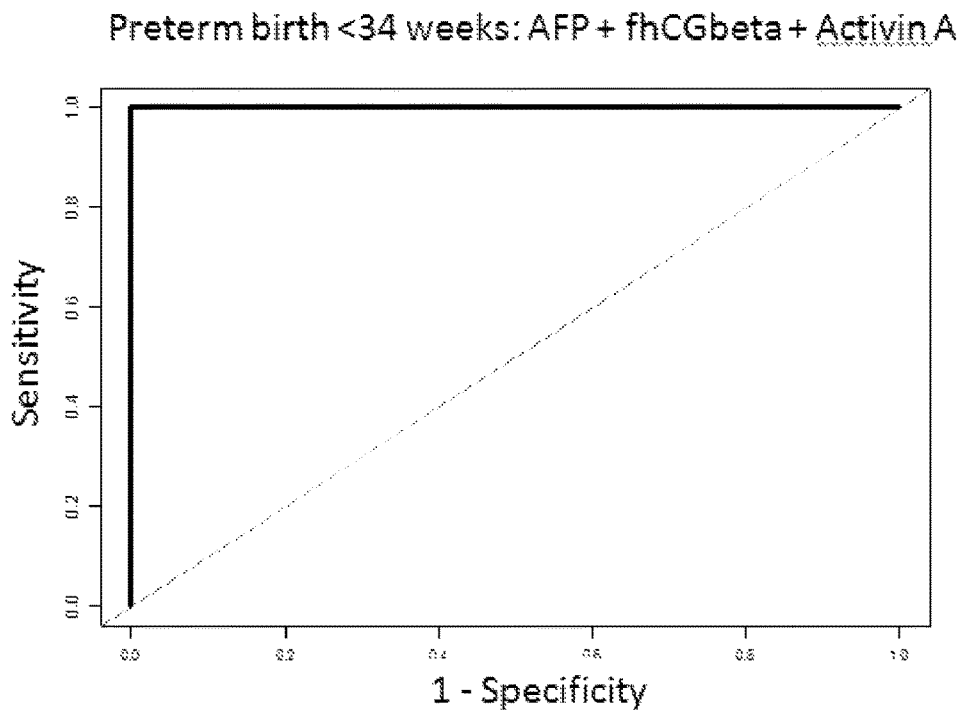

The present description relates to methods, kits and apparatus for determining the risk of preterm birth (PTB) in a pregnant individual. Specifically, provided is a method for determining risk of preterm birth (PTB) in a pregnant individual that involves measuring in a biological sample obtained from the pregnant individual levels of biomarkers AFP and free hCGbeta, and determining at least one additional measurement selected from the level of a biomarker selected from the group of FSTL3, sTNR1, PIGF2, Activin A, uE3, sP-selectin, and cervical length of the pregnant individual; and using this information to determine the risk of the pregnant individual developing PTB. The Examples herein demonstrate that the predictive power of AFP and fhCGbeta for determining risk of PTB are markedly improved by further combining one of the following markers: FSTL3, sTNFR1, PIGF-2, Activin A, uE3 and sP-selectin, and/or a measurement of cervical length. This is especially true of the prediction of early PTB, where a combination of AFP and fhCGbeta detects 14% of PTB cases at 1% false positive rate (FPR) whereas a combination of AFP and fhCGbeta together with either FSTL3, sTNFR1 or Activin A detects 100% of early PTB cases at 1% FPR.

Previous studies have shown that AFT and fhCGbeta can be used for predicting PTB. Spencer, K. Prenatal Diagnosis 2000; 20:652-656 has shown that high serum alpha-fetoprotein (AFP) level together with low or high free β-human chorionic gonadotrophin (free hCGbeta), both measured at 14-18 weeks, indicates an increased risk of preterm birth (PTB). Smith et al. Journal of Epidemiology 2006; 35:1169-1177 has shown that the risk of spontaneous preterm delivery among nulliparous women with no previous births is associated with a number of maternal characteristics and with second trimester maternal serum levels of placentally derived proteins. High levels of hCG, maternal age<20 and two or more previous miscarriages were more strongly associated with extreme preterm delivery than moderate or mild preterm delivery. However, models using maternal characteristics and second trimester serum screening results did not have predictive ability for spontaneous preterm birth, which would allow useful population-based screening.

The technology described herein allows the user to reliably predict PTB, including early PTB (delivery before 34 weeks of gestation), using a biological sample obtained from a pregnant individual, such as serum, plasma or vaginocervical material. The samples can be obtained during second or third trimester of pregnancy, such as during weeks 14-16.

The methods for determining the risk of preterm birth in a pregnant individual involve using a biological sample from the pregnant individual. The biological sample can be any body fluid or tissue sample that contains the selected biochemical markers. The choice of biological sample can often depend on the assay formats available in a particular clinical laboratory for testing levels of markers. For example, some assay formats lack sensitivity needed for assaying whole blood, such that a clinical laboratory opts for testing a fraction of blood, such as serum, or using dried blood. Further, samples that have been preserved, such as by freezing or drying (e.g. on blood card format), are suitable for use in the methods described herein. Exemplary biological samples useful for the methods described herein include blood, purified blood products, (such as serum, plasma, etc.) urine, amniotic fluid, a chorionic villus biopsy, a placental biopsy and vaginocervical material, such as a cervical swab or fluid. This means that the method is carried out outside of the body of the pregnant woman (in vitro).

In some embodiments biological sample is selected from the group consisting of whole blood, plasma, serum and vaginocervical material, or biological sample is obtained from a fraction of whole blood, plasma, serum or vaginocervical material.

Typical assay formats for determining the level of polypeptide and other biomarkers in a sample involve use of a control polypeptide, especially when quantitating levels of such polypeptides. Commercially available proteins and other biomarkers can be used as standards in assays measuring the level of biochemical markers. Alternatively, method for expressing protein, such as in prokaryotic and eukaryotic systems, and for synthesizing polypeptides are well known. Full length proteins and fragments thereof can be used as standards for quantitative determination of biomarkers in a sample obtained from a pregnant individual.

To determine whether the amount of biochemical markers is greater than or less than normal, the normal amount of biochemical marker present in a biological sample from a relevant population is determined. The relevant population can be defined based on any characteristics that can affect normal (unaffected) amounts of markers. For determining risk of PTB, the relevant population can be established on the basis of low risk of preterm birth. Once the normal marker amounts are known, the determined marker amounts can be compared and the significance of the difference determined using standard statistical methods. When there is a statistically significant difference between the determined marker amount and the normal amount there is a significant risk for preterm birth of the tested individual.

The level of a biochemical marker present in a sample can be determined using any assay format suitable for measuring proteins in biological samples. A common assay format for this purpose is the immunoassay, including, for example, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); dissociation-enhanced lanthanide fluorescent immunoassay (DELFIA) and chemiluminescence assays (CL). Amounts of biochemical markers present in a biological sample may also be measured by mass spectrometry, for example, by relative or absolute quantitative mass spectrometry using labelled or unlabelled proteins.

Cervical length is measured according to current clinical best practice. Cervical length can be measured, for example, by a transabdominal ultrasound and/or a transvaginal ultrasound. The normal length of cervix is 3 to 5 cm, whereas shorter length is suggestive of increased risk for PTB.

As is described herein, the risk of preterm birth can be determined based on the amounts of the biomarkers AFP and free hCGbeta, and at least one biochemical marker selected from FSTL3, sTNFR1, PIGF-2, Activin A, Ue3 and sP-selectin, optionally together with measuring biophysical marker cervical length; or measuring biochemical markers AFP and free hCGbeta, and cervical length, said biochemical markers being present in a biological sample taken from the individual. Additional biochemical markers, biophysical markers, patient history parameters, patient demographic parameters, and/or biophysical measurements can also be used when determining the risk of preterm birth according to methods, kits and apparatus described herein.

Biochemical or biophysical markers are called here together also "biomarkers". As described herein, statistical analysis of a clinical population was performed, revealing each of biochemical markers AFP and free hCGbeta, and at least one biomarker selected from FSTL3, sTNFR1, PlGF-2, Activin A, Ue3 and sP-selectin, and optionally cervical length measurement; or measuring biochemical markers AFP and free hCGbeta, and cervical length, were remarkably effective for determining risk of preterm birth with clinically acceptable detection and false positive rates. As used herein the "% detection" in the percentage-expressed proportion of affected (for example, PTB positive) individuals with a positive result. The "% false positive detection" is the percentage-expressed proportion of unaffected individuals with a positive result. The predictive power of a marker or combination thereof is commonly expressed in terms of the detection rate for a given false positive rate.

To improve risk evaluation, in some implementations, a number of risk-related factors may be considered in combination with the evaluation of biochemical marker levels of an individual. For example, an algorithm for predicting risk of PTB may involve one or more of additional biochemical markers, patient history parameters, patient demographic parameters, and/or patient biophysical measurements. Patient history parameters, in some examples, can include parity, smoking history, past medical conditions, and family history of preterm birth. Patient demographic parameters, in some examples, can include age, ethnicity, current medications, and vegetarianism. Patient biophysical measurements, in some examples, may include cervical length, body weight, body mass index (BMI), blood pressure, heart rate, cholesterol levels, triglyceride levels, medical conditions, and gestational age.

In certain circumstances, biological samples can be collected on more than one occasion from a pregnant individual, for example, when the patient comes to routine prenatal tests, monitoring for development of preterm birth due to a priori risk, presentation of symptoms and/or other factors. The methods for determining risk of preterm birth described herein can also be used for monitoring a pregnant individual who is undergoing a therapy or treatment for a preterm birth. If desired, testing of biochemical and/or biophysical markers can be carried out in a home setting, such as by using dipstick biochemical test formats for home use and a personal computer device for interpreting the results.

The present disclosure is based on studies, where by "an increased risk of preterm birth", was meant that the likelihood that the pregnant individual will experience preterm birth, including early preterm birth, is on a level which is higher than in a control group of pregnant individuals who did not experience preterm birth.

Previously published studies have shown that an increased level of AFP (MoM>2.0) and increased or decreased free hCGbeta (MoM >2.0 or <0.5) indicates higher risk for development of early preterm birth.

The abbreviation "AFP" means alpha-fetoprotein.

The abbreviation "hCGbeta" means beta subunit of human chorionic gonadotrophin.

The abbreviation "FSTL3" means follistatin like 3.

The abbreviation "sTNFR1" means soluble tumor necrosis factor receptor 1.

The abbreviation "PlGF-2" means isoform 2 of placenta growth factor.

The abbreviation "uE3" means unconjugated estriol.

The abbreviation "sP-selectin" means soluble P-selectin.

Activin A is a glycoprotein hormone produced by many tissues but in normal pregnancy the main source is the placenta.

The biochemical markers can be measured by using well known protein detection methods, for example commercially available immunoassay kits.

The methods for determining the risk of preterm birth in a pregnant individual involve determining the amount of biomarkers AFP and free hCGbeta, and at least one biomarker selected from FSTL3, sTNFR1, PlGF-2, Activin A, Ue3 and sP-selectin, and optionally measuring cervical length; or determining the amount of biomarkers AFP and free hCGbeta and measuring the cervical length. The screening performance will be improved, as reflected by increased detection rates and lower false positive rates, relative to laboratory tests that employ only AFP and free hCGbeta.

The detection of the markers AFP and free hCGbeta, and at least one biomarker selected from FSTL3, sTNFR1, PlGF-2, Activin A, Ue3 and sP-selectin can be combined with any other suitable biochemical markers or other indicators used for assessing the risk of preterm birth.

The detection of biochemical markers AFP and free hCGbeta, and at least one biomarker selected from FSTL3, sTNFR1, PlGF-2, Activin A, Ue3 and sP-selectin can be combined also with any suitable biophysical markers for assessing the risk of preterm birth. Such biophysical markers are for example cervical length, blood pressure, and pulse.

Furthermore, the detection of biochemical markers AFP and free hCGbeta and measuring of biophysical marker cervical length can be combined with any other suitable biochemical or biophysical markers.

As used herein, "maternal history factors" refers to set of maternal characteristics expected to have impact on the biochemical and biophysical marker levels measured. In the field of adverse pregnancy outcome screening, maternal history is generally accepted to comprise at least maternal age, weeks of gestation, racial origin, cigarette smoking during pregnancy, method of conception, medical history, medication, parity, obstetric history and BMI. To improve reliability of risk calculations, these factors can be included into algorithms. Inclusion of maternal history improves the detection rates of screens during pregnancy. To determine the factors usable in algorithms, maternal history is collected from a population from which relation of a biochemical marker and adverse pregnancy outcomes is determined. Collection is typically based on a questionnaire completed by the individual herself, which is generally reviewed by a health-care professional together with the patient. When assessing the risk for an individual, same characteristics are collected from her and taken into account when performing the risk determination. The collected or measured maternal weight and height can be converted into body mass index (BMI) in $Kg/m^2$.

The Example below includes descriptions of statistical analysis of clinical studies relating to use of biomarkers to determine risk of PTB. The risk that a pregnant individual has risk of preterm birth can be determined from biochemical marker levels using statistical analysis based on clinical data collected in a patient population study. There are multiple statistical methods for combining parameters that characterize the pregnant individual, such as levels of biochemical markers and/or biophysical markers, to obtain a risk estimate. The likelihood method (Palomaki and Haddow, Am. J. Obstet. Gynecol. 156, 460-3 (1987)), the linear discriminant function method (Norgarrd-Pedersen et al.

Clin. Genet. 37, 35-43 (1990)) and multiple logistic regression analysis are commonly used for this purpose.

As such, the methods described herein for determining risk can be based on use of well-known statistical methods, in which a cutoff or a MoM is used to determine risk. It is understood that equivalent well-known statistical approaches can be taken to assess risks of medical conditions.

The basic principle of the likelihood method is that the population distributions for a parameter (such as the level of a biochemical marker) are known for the 'unaffected' and 'affected' groups. Thus, for any given parameter (such as the amount of marker), the likelihood of membership of the 'unaffected' and 'affected' groups can be calculated. The 'likelihood ratio' is the ratio of the heights calculated using 'unaffected' and 'affected' population distributions, and is an expression of the increased risk of preterm birth, with respect to a prior risk. The likelihood of having PTB can be directly modelled using multivariate logistic regression models or the likelihood can be modelled by first modelling the distributions. Distributions can be modelled using a multivariate Gaussian distributions or their combinations. In current chromosomal abnormality screening practice, biochemical marker values are being referred to median values to produce adjusted multiple of the median (MoM) values to standardize for factors such as assay, gestation, maternal weight, smoking status, and the like. This is done, for example, because the amounts of biochemical markers in the individual's body change with gestation, in order to visualize the effect of the biomarker value in affected population, the marker value is normalized by mean or median of the unaffected population as the function of gestational age. The value of MoM for a sample is the ratio of the biochemical marker value to the population median value at the same gestational age (or other parameter). Consequently, calculating risk using two or more biochemical markers requires first that individual likelihood ratios be defined for each of the markers (first corrected for one or more factors such as one or more biophysical markers, maternal history parameters, maternal demographic parameters, and/or maternal biophysical measurements) and then combined (e.g. multiplied) together. In some implementations, an additional factor is introduced in the calculation to account for the extent of overlap of information (correlation) of the two or more individual biochemical markers. For example, r-values may be used to express the correlation between parameters, such as our example of two individual biochemical markers. In an alternative personalized approach, it is understood that comparison of biomarker level and a corresponding predetermined control level encompasses a comparison of a multidimensional representation of a combination of two or more biomarker levels.

The methods described herein for determining the risk of preterm birth in a pregnant individual can be practiced using a sample obtained from the woman during the second or third trimester of pregnancy. In a specific embodiment, the sample is obtained during first trimester of pregnancy, such as during weeks 11 to 13. In another specific embodiment the sample is obtained during second trimester of pregnancy, such as during weeks 14 to 16. In a further specific embodiment, during weeks 17-20, of gestational age. In an embodiment, one or more samples can be obtained from the woman at one or more trimesters of pregnancy.

Optionally, one sample can be obtained during the first trimester or second trimester and another in a later stage of pregnancy, such as during the third trimester of the pregnancy. The ability to detect a high risk of preterm birth within the first or second trimester of pregnancy provides more time for a health care provider to provide prevention strategies for the pregnant woman. It is often desirable to complete a risk assessment early in pregnancy, to allow time for measures for preventing or retarding the preterm birth.

Biophysical markers, such as cervical length, are measured at the same stages of pregnancy as the above biochemical markers.

Typically, results obtained from measurement of levels of biochemical or biophysical markers (called here also together biomarkers) are processed using algorithms run on a computer. A computer program which when executed on a computer causes the computer to perform a process for determining risk of preterm birth, or early preterm birth in a pregnant individual. The process can involve inputting a measurement to retrieve the biomarker levels, wherein each biomarker level of the biomarker levels corresponds to a biochemical marker tested for using the in vitro diagnostics kit or measured or otherwise obtained biophysical marker, and wherein the retrieved biomarker levels comprises a biomarker AFP and free hCGbeta, and at least one biomarker selected from the group of FSTL3, sTNFR1, PlGF-2, Activin A, Ue3 and sP-selectin and optionally measurement of cervical length; or wherein the retrieved biomarker levels comprises a biomarker AFP, free hCGbeta and cervical length; calculate a risk assessment score corresponding to a relative risk of the pregnant individual developing PTB, wherein the risk assessment score is based in part upon a comparison of the biomarker level and a corresponding predetermined control level, ratio of values or cut-off value.

The computer program can involve inputting a measurement of at least one biomarker obtained by determining one or more biophysical markers of the subject; comparing the one or more biophysical markers of the subject with the same biophysical marker in a control subject, wherein an increased or decreased measure of the one or more biophysical marker in the subject relative to the control is indicative of an increased risk of preterm birth, and determining a quantitative estimate of risk of preterm birth based on the result of the compared one or more biochemical marker and the compared one or more biophysical marker. In particular embodiments, the biophysical marker can be selected from cervical length, blood pressure and pulse.

In the computer program, the process can also include determining the quantitative estimate of risk of preterm birth comprises determining the likelihood of preterm birth using a multivariate analysis, and wherein the multivariate analysis comprises using levels of the biochemical markers and distribution parameters derived from a set of control reference data. The multivariate analysis can be a multivariate Gaussian analysis.

The present disclosure thus provides a method for determining the risk of preterm birth (PTB) in a pregnant individual, which comprises measuring from the pregnant individual biochemical markers and optionally biophysical markers by a) measuring in a biological sample obtained from the pregnant individual levels of biomarkers AFP and free hCGbeta, and at least one biomarker selected from the group consisting of FSTL3, sTNR1, PlGF2, Activin A, uE3 and sP-selectin; or b) measuring in a biological sample obtained from the pregnant individual levels of biomarkers AFP and free hCGbeta, and measuring the cervical length of the pregnant individual; and determining the risk of the pregnant individual developing PTB by using the measured biomarkers.

The risk that a pregnant individual has risk of preterm birth can be determined from biochemical or biophysical marker levels using statistical analysis based on clinical data collected in a patient population study. There are multiple statistical methods for combining parameters that characterize the pregnant individual, such as levels of biochemical markers and/or biophysical markers, to obtain a risk estimate. The likelihood method (Palomaki and Haddow, Am. J. Obstet. Gynecol. 156, 460-3 (1987)), the linear discriminant function method (Norgarrd-Pedersen et al. Clin. Genet. 37, 35-43 (1990)) and multiple logistic regression analysis are commonly used for this purpose.

The determination of the risk of PTB can be carried out by using the models, which have been established in finding the markers, or the functions, which include the following information of the models: the dependence between marker levels and likelihood and/or directly or indirectly uses the information of correlation structure or part of it with the likelihood. Correlation structure can be utilized for example by expressing the likelihood as the function of marker's ratios or products. The information of the model can also be expressed for example in a format of decision tree. The determination of risk may comprise deriving the likelihood ratio using a multivariate analysis based on distribution of parameters from a set of reference data.

Calculation of risk from the measured marker levels can be based on the observed relative frequency distribution on marker levels in the affected and unaffected pregnancies. Any known statistical techniques may be used in the calculations.

The estimation of risk may consist of multiplying the likelihood ratio by the background risk of PTB. The estimated risk is classified as screen-positive or screen negative based on a comparison with the predetermined risk cut-off. The value of the risk cut-off may be altered to vary the detection rate and false positive rate.

The present disclosure is not limited to the use specific statistical methods, models or functions, but encompasses several different determination methods. The present risk assessment is based on the use of the disclosed biomarkers which were shown to predict PTB in a reliable manner.

As is disclosed herein, the risk of preterm birth can be determined based on the amounts of the biochemical markers AFP and free hCGbeta, and at least one biochemical marker selected from FSTL3, sTNFR1, PlGF-2, Activin A, Ue3 and sP-selectin, advantageously selected from FSTL3 and Activin A, optionally together with biophysical marker cervical length; or biochemical markers AFP and free hCGbeta, and cervical length, said biochemical markers being present in a biological sample taken from the individual. Additional biochemical markers, biophysical markers, patient history parameters, patient demographic parameters, and/or biophysical measurements can also be used when determining the risk of preterm birth according to methods, kits and apparatus disclosed herein.

To improve risk evaluation, in some implementations, a number of risk-related factors may be considered in combination with the evaluation of biochemical marker levels of an individual. For example, an algorithm for predicting risk of PTB may involve one or more of additional biochemical markers, patient history parameters, patient demographic parameters, and/or patient biophysical measurements. Patient history parameters, in some examples, can include parity, smoking history, past medical conditions, and family history of preterm birth. Patient demographic parameters, in some examples, can include age, ethnicity, current medications, and vegetarianism. Patient biophysical measurements, in some examples, may include cervical length, body weight, body mass index (BMI), blood pressure, heart rate, cholesterol levels, triglyceride levels, medical conditions, and gestational age.

The method described herein can be employed using kits or commercial packages for assessing risk of preterm birth. According to one embodiment, an in vitro kit for determining the risk of preterm birth (PTB), comprises means, such as reagents, for assaying or detecting biomarkers AFP, free hCGbeta, and at least one biomarker selected from the group of FSTL3, sTNFR1, PlGF-2, Activin A, Ue3 and sP-selectin.

According to another embodiment, an in vitro kit for determining the risk of preterm birth (PTB) comprises means, such as reagents, for assaying or detecting biomarkers AFP, free hCGbeta, and at least one biomarker selected from the group of FSTL3 and Activin A.

In various other embodiments, the risk assessment further comprises measurement of cervical length.

In some embodiments for each measured biomarker a difference between the measured level and a corresponding predetermined control level is identified; and responsive to the identifying, a relative risk of the pregnant individual developing PTB is determined.

In some embodiments, the difference between the measured level and a corresponding predetermined control level can comprise at least one of a threshold value and a percentage difference.

In some embodiments, a ratio or other dependencies between the measured levels of biochemical markers can be calculated.

In some embodiments of the method, determining the risk of preterm birth in a pregnant individual, further comprises using maternal history factors.

According to one further embodiment, an in vitro kit for determining the risk of preterm birth (PTB), comprises means, such as reagents, for assaying or detecting biomarkers AFP and free hCGbeta. The risk assessment further comprises measurement of cervical length.

A reagent for assaying or detecting biomarkers described herein can be, for example, a detectable binding partner. In a further specific embodiment, a kit can further provide instructions for using the detectable binding partners in the determination. Reagent volumes, incubation times, reaction conditions etc. can be provided in the instructions. Such kits can include also one or more reagents for detecting the amount of biochemical markers in a biological sample from a pregnant individual, wherein the biochemical markers are AFP, free hCGbeta, and at least one biomarker selected from the group of FSTL3, sTNFR1, PlGF-2, Activin A, Ue3 and sP-selectin. Alternatively such kits include one or more reagents for assaying or detecting the amount of biochemical markers in a biological sample from a pregnant individual, wherein the biochemical markers are AFP, free hCGbeta. In some implementations, the kit may comprise one or more of coated plate, calibrators, instructions for carrying out the test, and software for analyzing biomarker level measurement results in relation to a particular pregnant individual.

Herein is provided, in one further aspect, an in vitro kit for determining the risk of preterm birth (PTB), comprising means, typically a test panel or panels, for assaying a biological sample from the pregnant individual for biomarkers AFP, free hCGbeta, and at least one biomarker selected from the group of FSTL3, sTNFR1, PlGF-2, Activin A, Ue3 and sP-selectin or an in vitro kit for determining the risk of preterm birth (PTB), comprising a means, typically test panel or panels, for assaying a biological sample from the pregnant individual for biomarkers AFP, free hCGbeta.

Herein is provided, in one further aspect, an apparatus for predicting risk of preterm birth (PTB), comprising data input means for inputting a measurement of a biological sample of the pregnant individual for biomarkers AFP and free hCGbeta, and at least one biomarker selected from the group of FSTL3, sTNR1, PIGF2, Activin A, Ue3 and sP-selectin; or for biomarkers AFP and free hCGbeta and measurement of biophysical marker cervical length; and calculation means for determining the risk of PTB using the input levels of the said biomarkers.

The calculation means may be arranged to determine the risk of PTB by deriving the likelihood ratio for PTB using a multivariate analysis based on distribution parameters derived from a set of reference data.

Herein is provided, in one further aspect, a kit for predicting risk of preterm birth (PTB), comprising an in vitro kit for determining the risk of preterm birth (PTB), comprising a test panel or panels for biomarkers AFP and free hCGbeta, and at least one biomarker selected from the group of FSTL3, sTNFR1, PIGF-2, Activin A, uE3 and sP-selectin;

or an in vitro kit for determining the risk of preterm birth (PTB), comprising a test panel for biomarkers AFP, free hCGbeta and measuring cervical length;

a non-transitory computer-readable medium having instructions stored thereon, wherein the instructions, when executed by a prosessor, cause the processor to:

retrieve the biomarker levels, wherein each biomarker level of the biomarker levels corresponds to a biochemical marker tested for using the in vitro diagnostics kit, and wherein the retrieved biomarker levels comprises a biomarker AFP, free hCGbeta, and at least one biomarker selected from the group of FSTL3, sTNFR1, PIGF-2, Activin A, uE3 and sP-selectin and cervical length measurement result; or wherein the retrieved biomarker levels comprises a biomarker AFP, free hCGbeta and a measurement of cervical length measurement;

The kit can be used to determine a risk assessment score corresponding to a relative risk of the pregnant individual developing PTB, wherein the risk assessment score is based in part upon a comparison of the biomarker level and a corresponding predetermined control level or cut-off value.

The apparatus or system may comprise a non-transitory computer-readable medium having instructions stored thereon, wherein the instructions, when executed by a prosessor, cause the processor to: retrieve the biomarker levels, wherein each biomarker level of the biomarker levels corresponds to a biochemical marker tested for using the in vitro diagnostics kit, and wherein the retrieved biomarker levels comprises a biomarker AFP, free hCGbeta, and at least one biomarker selected from the group of FSTL3, sTNFR1, PIGF-2, Activin A and uE3 and sP-selectin; or comprises a biomarker selected from AFP and free hCGbeta. In addition, or alternatively, the screening performance of the mentioned biomarkers can be improved by combining them with cervical length measurement. The apparatus comprises also a calculation of a risk assessment score corresponding to a relative risk of the pregnant individual for PTB, wherein the risk assessment score is based in part upon a comparison of the biomarker level and a corresponding predetermined control level or cut-off value.

The present disclosure is not limited to the use specific statistical methods, models or functions, but encompasses several different determination methods. The disclosed risk assessment method is based on the use of the disclosed biomarkers which were shown to predict PTB in a reliable manner.

EXAMPLE 1

Results

Examination of Maternal Markers in Preterm Birth

Serum samples from week 14-16 DELFIA® Immunoassays or commercial ELISA (Activin A) were run. Results were converted into MoM values by normalizing concentrations with all significant background factors. Performance of marker combination to predict preterm birth was analysed with ROC plot (a receiver operating characteristics plot). FIGS. 1-10 are derived from this sample set. Comparison was done by comparing detection rate (sensitivity) at fixed (1% or 5%) false-positive rate (FPR) (1–specificity) (the calculation form is: 5% False-positive-rate (1–0.95=0.05). 1=100%, Specificity=95%, FPR=5%). AFP and fhCGB was measured with dual kit (B067-101) from PerkinElmer. FSTL-3, sTNFR1, Activin A assays used were custom research assays developed on DELFIA technology using commercial antibodies and antigens from R&D Systems. PIGF-2 a custom research assays developed on DELFIA technology using custom antibodies (AbD Serotec) and commercial antigen (R&D Systems).

TABLE 1

| Serum sample GA = 14-16 wks | n |
|---|---|
| Control samples (normal pregnancies) | 97 |
| Preterm birth GA < 37 | 51 |
| Preterm birth GA = 34-37 wk | 42 |
| Early Preterm birth GA < 34 | 9 |

TABLE 2

| Preterm birth GA < 37 wk | DR @ 5% FPR |
|---|---|
| FSTL3 | 5 |
| sTNFR1 | 7 |
| Activin A | 10 |
| PIGF2 | 17 |
| AFP + fhCGbeta | 29 |
| AFP + fhCGbeta + FSTL3 | 40 |
| AFP + fhCGbeta + sTNFR1 | 33 |
| AFP + fhCGbeta + Activin A | 33 |
| AFP + fhCGbeta + PIGF2 | 29 |

TABLE 3

| Preterm birth GA = 34-36 wk | DR @ 5% FPR |
|---|---|
| FSTL3 | 6 |
| sTNFR1 | 6 |
| PIGF2 | 17 |
| AFP + fhCGbeta | 31 |
| AFP + fhCGbeta + FSTL3 | 37 |
| AFP + fhCGbeta + sTNFR1 | 34 |
| AFP + fhCGbeta + PIGF2 | 40 |

TABLE 4

| Early Preterm birth GA < 34 wk | DR @ 1% FPR | DR @ 5% FPR |
|---|---|---|
| FSTL3 | 0 | 0 |
| sTNFR1 | 14 | 29 |
| Activin A | 0 | 29 |
| PIGF2 | 0 | 14 |
| AFP + fhCGbeta | 14 | 86 |
| AFP + fhCGbeta + FSTL3 | 100 | 100 |
| AFP + fhCGbeta + sTNFR1 | 100 | 100 |

TABLE 4-continued

| Early Preterm birth GA < 34 wk | DR @ 1% FPR | DR @ 5% FPR |
|---|---|---|
| AFP + fhCGbeta + Activin A | 100 | 100 |
| AFP + fhCGbeta + PlGF2 | 71 | 86 |

EXAMPLE 2

Examination of Maternal Markers in Preterm Birth

Figure 11:
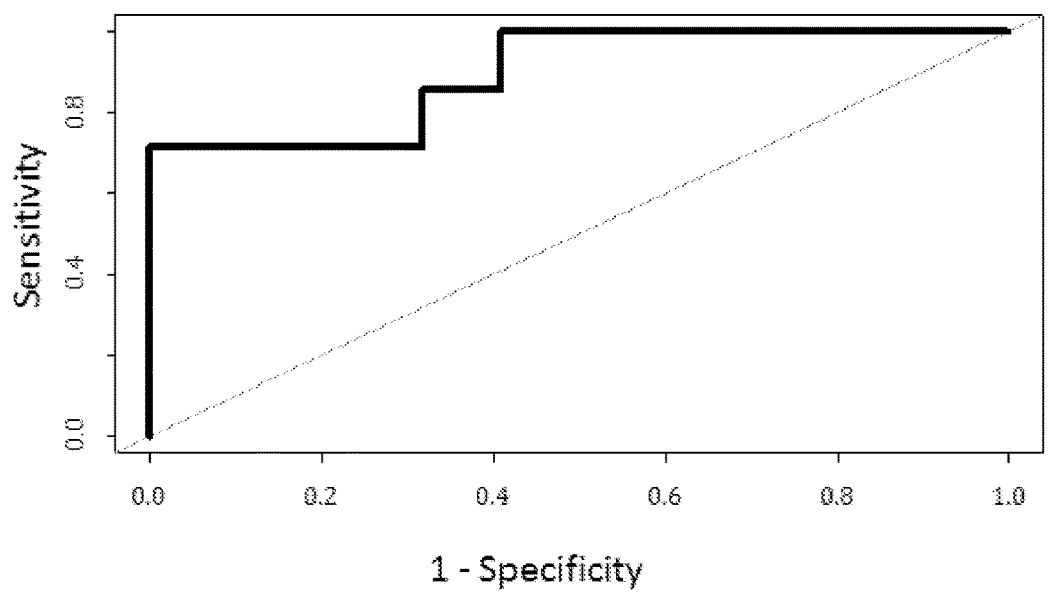
Figure 12:
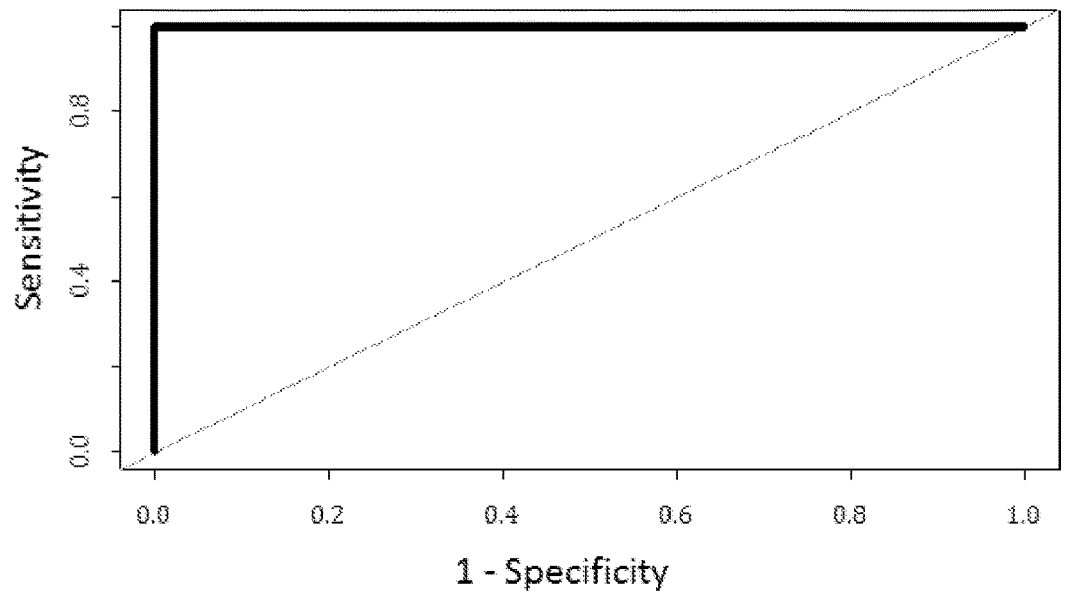
FIG. 12 describes the screening performance of AFP, fhCGbeta and cervical length in all spontaneous preterm birth pregnancies.

Serum samples, wk 16, high risk women with previous preterm birth, measures AFP and free hCGbeta and cervical length. Biochemical results were converted into MoM values by normalizing concentrations with all significant background factors. Cervical length was analysed in similar way in this performance analysis. Normally a low percentile cut-off is used for cervical length to determine high risk pregnancies. Performance of marker combination to predict preterm birth was analysed with ROC plot (FIGS. 11-12). Comparison was done by comparing detection rate (sensitivity) at fixed (5%) false-positive rate (FPR) (1−specificity).

AFP and fhCGB was measured with dual kit (B067-101) from PerkinElmer.

Table 5: ROC plot tells how big portion of pregnancies, subsequently affected by PTB, are identified with certain false-positive rate. This means that if detection rate is 0.75 (=75%) and used false positive rate is 1−0.95 (=5%), 75% of all PTB pregnancies are identified by following 5% of all pregnancies in the screened population.

|  | DR @ 5% FPR |
|---|---|
| Spontaneous Preterm birth GA < 37 wk |  |
| AFP + fhCGbeta | 50 |
| AFP + fhCGbeta + Cervical length | 100 |
| All Preterm birth GA < 37 wk |  |
| AFP + fhCGbeta | 30 |
| AFP + fhCGbeta + Cervical length | 75 |

EXAMPLE 3

Examination of Maternal Markers in Preterm Birth.

Figure 13:
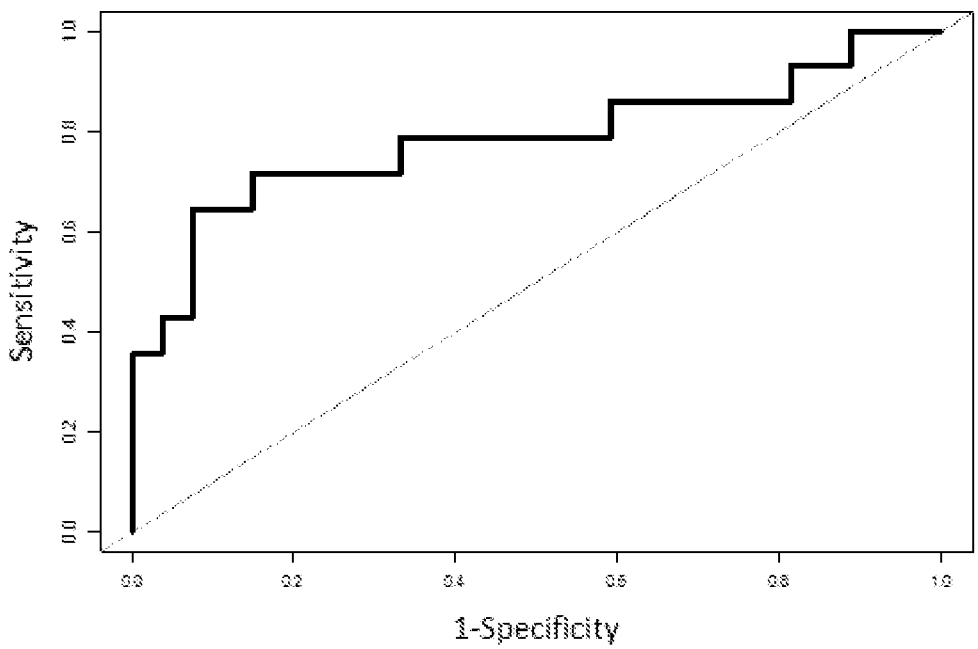
FIG. 13 describes the screening performance of AFP, fhCGbeta and sP-selectin. Extremely early Preterm birth, GA<29 weeks FIG. 14 describes the screening performance of AFP, fhCGbeta and uE3. Extremely early Preterm birth, GA<29 weeks
Figure 14:
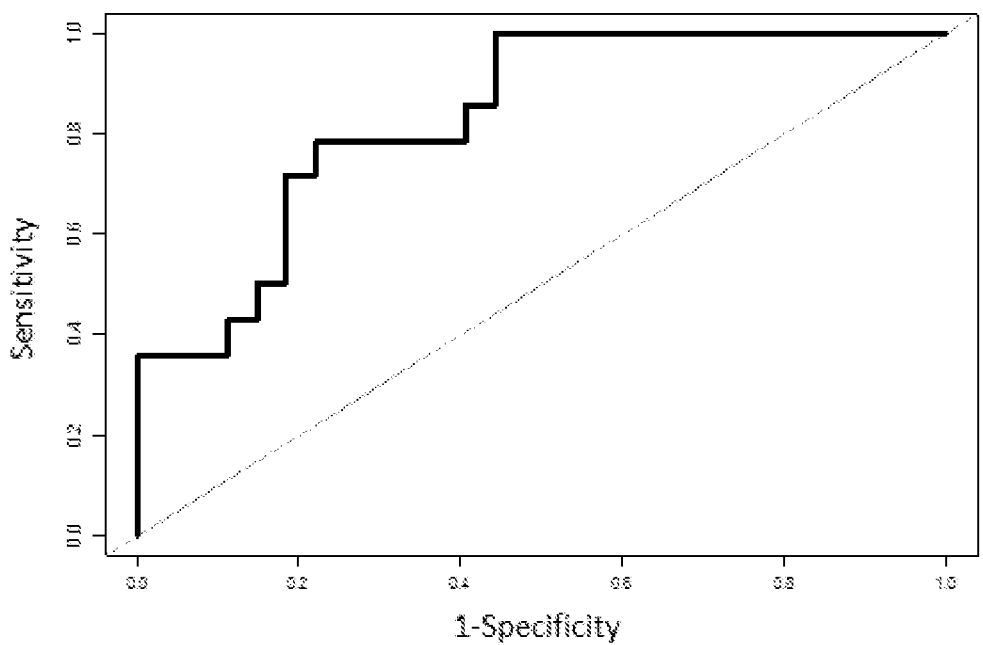

Serum samples, wk 18-22 and wk 14-16, measured AFP and free hCGbeta together with sP-selectin or uE3 (unconjugated estriol). Results were converted into MoM values by normalizing concentrations with all significant background factors. Performance of marker combination to predict preterm birth was analysed with ROC plot. Comparison was done by comparing area-undercurve of a ROC plot and detection rates (sensitivity) at fixed (5% and 10%) false-positive rates (FPR) (1−specificity) (FIGS. 13-14). (ROC means receiver operating characteristics; AUC means area under the curve)

AFP and fhCGB was measured with dual kit (B067-101) from PerkinElmer. uE3 was measured using a kit from PerkinElmer B083-301. sP-selectin assay used was a custom research assays developed on DELFIA technology using commercial antibodies and antigens from R&D Systems.

TABLE 6

Samples taken 18-22 wk from 433 control and 87 moderate, 42 very early and 49 extremely early PTB samples.

| Outcome | Marker Combination | ROC AUC |
|---|---|---|
| Extremely early PTB before wk 28 | AFP + fhCGbeta + sP-selectin | 0.64 |
|  | AFP + fhCGbeta + uE3 | 0.62 |
|  | AFP + fhCGbeta | 0.61 |
| Very early PTB wk 29-33 | AFP + fhCGbeta + sP-selectin | 0.63 |
|  | AFP + fhCGbeta + uE3 | 0.65 |
|  | AFP + fhCGbeta | 0.61 |
| Moderately early PTB wk 34-36 | AFP + fhCGbeta + sP-selectin | 0.61 |
|  | AFP + fhCGbeta + uE3 | 0.65 |
|  | AFP + fhCGbeta | 0.58 |

TABLE 7

Samples taken 14-16 wk from 27 control and 14 extremely early (delivery before GA week 28) PTB samples.

| Outcome | Marker Combination | ROC AUC | DR & 5% FPR | DR & 10% FPR |
|---|---|---|---|---|
| Extremely early PTB before wk 28 | AFP + fhCGbeta + sP-selectin | 0.78 | 0.43 | 0.64 |
|  | AFP + fhCGbeta + uE3 | 0.83 | 0.36 | 0.36 |
|  | AFP + fhCGbeta | 0.67 | 0.43 | 0.43 |

The invention claimed is:

1. A method of treating a pregnant individual based on a detected increased risk of preterm birth (PTB), the method comprising:
   i) measuring in a biological sample obtained from the pregnant individual during gestational weeks 11 to 20, levels of biomarkers AFP (alpha-fetoprotein) and free hCGbeta (beta human chorionic gonadotropin);
   ii) selecting at least one additional biomarker from FSTL3 (follistatin like 3), PlGF2 (placental growth factor), and Activin A, and measuring a level of the selected at least one biomarker in the biological sample;
   iii) measuring cervical length of the pregnant individual; and
   iv) detecting whether the pregnant individual is at an increased risk for PTB wherein the detecting is based on: (a) determining that the combined level of the biomarkers measured in i) and ii) are increased or decreased as compared to predetermined control levels of the biomarkers measured from individuals with normal pregnancies; and, (b) determining that the pregnant individual's cervical length as measured in iii) is decreased when compared to predetermined control cervical lengths from individuals with normal pregnancies,
   wherein the detection rate for increased risk for preterm birth is between 70-100% with a false positive rate of not more than 1%; and,
   v) providing to the pregnant individual having been detected to be at increased risk for PTB, a treatment to prevent or retard the PTB.

2. The method according to claim 1, wherein in ii) the level of a FSTL3 or Activin A is measured.

3. The method according to claim 1, wherein said biological sample is selected from the group consisting of whole blood, plasma, serum, urine, vaginocervical material, and a fraction of whole blood, plasma, serum, urine or vaginocervical material.

4. The method according to claim 1, wherein the biological sample is obtained during weeks 11 to 13.

5. The method according to claim 1, wherein the biological sample is obtained during weeks 14 to 16.

6. The method according to claim 1, wherein the biological sample is obtained during weeks 17 to 20.

* * * * *